United States Patent [19]

Spivack et al.

[11] 4,318,845

[45] Mar. 9, 1982

[54] ALKANOLAMINE ESTERS OF 1,1'-BIPHENYL-2,2'-DIYL-AND ALKYLIDENE-1,1'-BIPHENYL-2,2'-DIYL-CYCLIC PHOSPHITES

[75] Inventors: John D. Spivack, Spring Valley; Martin Dexter, Briarcliff Manor; Stephen D. Pastor, Spring Valley, all of N.Y.

[73] Assignee: Ciba-Geigy Corporation, Ardsley, N.Y.

[21] Appl. No.: 209,786

[22] Filed: Nov. 24, 1980

[51] Int. Cl.³ .................... C08K 5/52; C07D 295/08; C07D 221/00

[52] U.S. Cl. ................ 524/91; 260/927 R; 260/937; 544/84; 544/157; 544/232; 546/22; 524/99; 524/100; 524/101; 524/117; 524/119

[58] Field of Search .................. 260/927 R, 936, 937, 260/45.8 R, 45.8 NE, 45.8 N, 45.8 NZ; 544/84, 157, 232; 546/22

[56] References Cited

U.S. PATENT DOCUMENTS

| | | | |
|---|---|---|---|
| 4,185,006 | 1/1980 | Rasberger et al. | 260/927 R |
| 4,210,576 | 7/1980 | Di Battista et al. | 546/22 |
| 4,252,750 | 2/1981 | Buysch et al. | 260/927 R |
| 4,259,492 | 3/1981 | Rasberger | 260/927 R |

*Primary Examiner*—V. P. Hoke
*Attorney, Agent, or Firm*—Harry Falber

[57] ABSTRACT

The title compounds are prepared by reacting alkylated 1,1'-biphenyl-2,2'-diol or alkylated 2,2'-alkylidene-bis-phenol with phosphorus trichloride in an organic solvent and then reacting the intermediate phosphorochlorodite with an alkanolamine. Said phosphites are useful as stabilizers of organic polymers and lubricating oils, especially as processing stabilizers for polyolefins, elastomers, polyesters and polycarbonates.

24 Claims, No Drawings

ALKANOLAMINE ESTERS OF 1,1'-BIPHENYL-2,2'-DIYL-AND ALKYLIDENE-1,1'-BIPHENYL-2,2'-DIYL-CYCLIC PHOSPHITES

Organic polymeric materials such as plastics and resins, and lubricating and mineral oils are subject to thermal, oxidative and photodegradation. A great variety of stabilizers are known in the art for stabilizing various substrates. Their effectiveness varies depending on the causes of degradation and the substrate stabilized. During the course of this work, it was discovered that stabilizers that are very effective long term antioxidants are relatively poor process stabilizers and do not protect the substrate against thermal degradation for a short time at relatively high process temperatures. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

The phosphites of this invention possess an unusual combination of desirable properties as compared to the prior art phosphites which makes these compounds particularly effective and useful as stabilizers.

Phosphites are disclosed in a number of publications. U.S. Pat. No. 4,196,117 discloses biphenyl-cyclic phosphites wherein the phosphorus atom is substituted by O- or S-hydrocarbyl or a hydrocarbyl biphenyl cyclic phosphite group. Soviet Union patent Nos. 378,389, 429,070 and 440,390 disclose the stabilization of various polymers with organic phosphites or mixtures including said phosphites wherein the phosphites are methylene-bisphenyl cyclic phosphites. Additional 1,1'-biphenyl-2,2'-diyl phosphites are disclosed in Chemical Abstracts, 68, 12597s (1968), 73, 15657a (1970) and 75, 130242q (1971). These various compounds are indicated to be stabilizers of various polymers. However, the instant alkanolamine esters are significantly more effective as process stabilizers, as color stabilizers and in resistance to hydrolysis.

In addition, alkanolamine phosphites and the stabilization of vinyl and vinylidene resins therewith are disclosed in U.S. Pat. No. 2,841,607. It is to be noted, however, that these phosphites are significantly distinct in structure from the instant compounds.

Accordingly, it is the primary object of this invention to provide biphenyl cyclic phosphite compounds which exhibit improved process stabilization performance as contrasted with previously known phosphite compounds.

Various other objects and advantages of this invention will become evident from the following description thereof.

The compounds of this invention correspond to the formula:

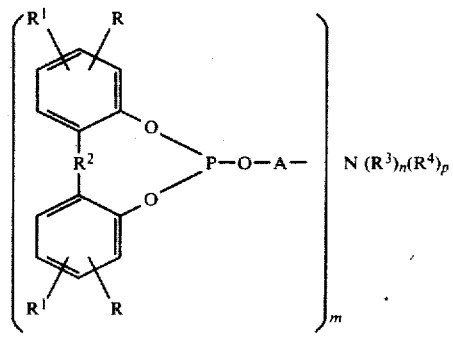

such that when m=1, n=1 and p=1 m=2, n=1 and p=0 m=3, n and p are zero, and wherein R is an alkyl group of 1 to 18 carbon atoms, $R^1$ is hydrogen or an alkyl group of 1 to 18 carbon atoms;

$R^2$ is a direct bond or lower alkylene of 1 to 12 carbon atoms;

A is alkylene of 1 to 6 carbon atoms or cycloalkylene of 5 to 6 carbon atoms;

$R^3$ is an alkyl of 1 to 18 carbon atoms, or

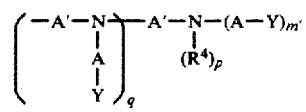

wherein Y is

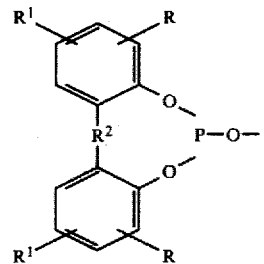

A' is alkylene of 1 to 6 carbon atoms or cycloalkylene of 5 to 6 carbon atoms, m' is 1 or 2, p is 0 or 1, and q is 0-5 with A, R, $R^1$, $R^2$ being as previously defined; provided that when p and q are 0, —N—A'—N can be a diazacycloalkyl group of 2 to 10 carbon atoms or, when m is 1 and p is 0, N-$R_3$ is an azacycloalkyl group of 2 to 10 carbon atoms or an azaoxacycloalkyl group of 3 to 7 carbon atoms; and $R^4$ is alkyl of 1 to 18 carbon atoms.

Preferred compounds within the above structure are those wherein R is in the ortho position to the phosphite oxygen in each of the phenyl rings.

The R and $R^1$ groups are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred. Also especially preferred is for the R¹ group to be in the para position to oxygen, particularly if R¹ is tert-alkyl.

Although R¹ can be hydrogen or alkyl of 1 to 18 carbons, preferably it is an alkyl group of 1 to 8 carbon atoms, either straight-chain or branched-chain. Especially preferred is tert-alkyl of 4 to 8 carbon atoms.

R² is preferably lower alkylene of the formula

wherein R⁵ and R⁶ are independently hydrogen, alkyl of 1 to 7 carbon atoms or aryl, provided that the total number of carbon atoms does not exceed 12. Typical aryl groups include phenyl, tolyl, mesityl, xylyl and 1- and 2-naphthyl.

The alkylated 1,1'-biphenyl-2,2'-diyl phosphites and 2,2'-alkylidene-bis(alkylphenyl) phosphites of this invention can be prepared by reacting an alkylated 2,2'-biphenol or an alkylated 2,2'-alkylidene-bis-phenol with phosphorus trichloride optionally in a solvent to give the corresponding phosphorochlorodite which in turn is reacted with a tertiary amino-alkoxide or -alkanol to yield the desired product. The solvent is preferably aromatic, such as benzene, toluene, xylene and the like. The reaction temperature ranges from room temperature to the reflux temperature of the reaction medium. Another method for preparing the compounds of this invention involves reacting the phosphorochlorodite with an appropriate alkanolamine in the presence of a proton acceptor such as a tertiary amine, for example, triethylamine or pyridine.

The starting materials needed to prepare these phosphites are items of commerce or can be prepared by known methods.

The alkanolamines used to prepare the compounds of this invention have the following formulae:

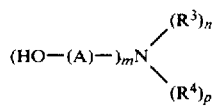

wherein R³ is alkyl of 1 to 18 carbon atoms and the other symbols have the meanings previously defined;

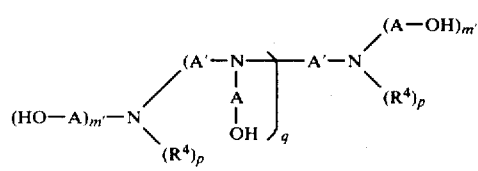

wherein A' is alkylene of 1 to 6 carbon atoms or cycloalkylene of 5 to 6 carbon atoms;

m' is 1 or 2;

p is 0 or 1; and q is 0-5;

provided that when p and q are zero, N'—A—N may also be piperazine-1,4-diyl; and

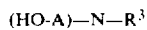

wherein N-R³ is an azacycloalkyl group of 2 to 10 carbon atoms or an azaoxacycloalkyl group of 3 to 7 carbon atoms.

Preferred examples of the intermediate alkanolamines include: N-2-hydroxyethyl aziridines, N-2-hydroxypropyl azetidines, N-2-hydroxyethyl pentamethyleneimine, N-2-hydroxyethyl hexamethyleneimine, N-3-hydroxypropyl octamethyleneimine and N-2-hydroxyethyl morpholine. Also preferred are hydroxyalkylated derivatives of alkyl- and cycloalkyl-amines as well as alkylenediamines and polyalkylene diamines, including N,N-dimethylethanolamine, N-methyliminodiethanol, N-butyliminodiethanol, N,N-dicyclohexyliminodiethanol, N-n-dodecylimino di-2-propanol, N-N-diethyl-N',N'-bis(2-hydroxypropyl) ethylenediamine, triethanolamine, N,N,N',N'-tetrakis-hydroxyethylethylenediamine, N,N',N'''-tris(2-hydroxyethyl)-N-n-octadecyl-1,3-diaminopropane, N,N'-bis(2-hydroxyethyl) piperazine, N-2-hydroxymethylpiperidine, N,N',N''-pentakis(2-hydroxyethyl) diethylenetriamine and N,N',N'', N'''-heptakis(2-hydroxypropyl) diethylenetriamine.

The synthesis of the compounds of the invention is represented by the following sequence of equations (in this instance depicted in terms of the preferred compounds):

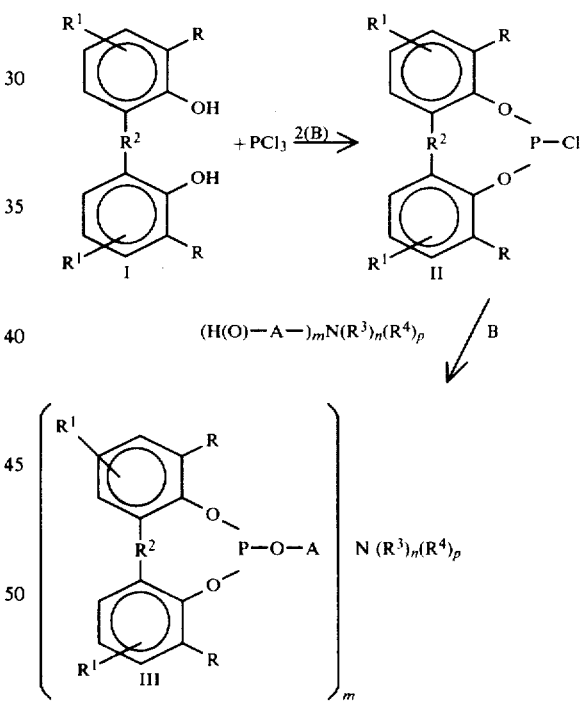

wherein B is a cyclic or acyclic tertiary amine used as a proton acceptor such as triethylamine and pyridine and the other symbols are as previously defined.

An analogous synthetic method would involve substituting alkali metal hydroxides or alkali metal carbonates for the tertiary amines in the synthetic scheme shown above. The above reaction sequences can be conducted to yield the compounds of this invention without isolation of the intermediate chlorodite II.

Compounds of this invention are particularly effective in stabilizing organic materials such as plastics, polymers and resins in addition to mineral and synthetic fluids such as lubricating oils, circulating oils, etc.

The compounds of this invention are particularly useful as stabilizers, especially for the protection of polyolefins, for instance, polyethylene, polypropylene, polyisobutylene, poly(butene-1), poly(pentene-1), poly(3-methylbutene-1), poly(4-methyl-pentene-1), various ethylene-propylene copolymers and the like.

Other substrates in which the compounds of this invention are particularly useful are polystyrene, including impact polystyrene, ABS resin, SBR, isoprene, as well as natural rubber, polyesters including polyethylene terephthalate and polybutylene terephthalate, including copolymers.

Polyurethanes, polycarbonates, polyamides such as nylon 6, 6/6 and the like as well as copolyamides and polysulfones are also stabilized.

In general, polymers which can be stabilized include:
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under (1), for example mixtures of polypropylene with polyethylene or with polyisobutylene.
3. Copolymer of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.
4. Polystyrene.
5. Random copolymers of styrene of α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from α,β-unsaturated acids and derivatives thereof, such as polyacrylates and polymethacrylates, polyacrylamides and polyacrylonitrile.
9. Copolymers from the monomers mentioned under (8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as a comonomer.
13. Polyphenylene oxides and sulfides.
14. Polyurethanes which are derived from polyethers, polyesters or polybutadienes with terminal hydroxyl groups on the one side and aliphatic or aromatic polyisocyanates on the other side, as well as precursors thereof.
15. Polyamides and copolyamides which are derived from diamines and dicarboxylic acids and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.
16. Polyureas, polyimides and polyamide-imides.
17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyetheresters derived from polyethers having hydroxyl end groups.
18. Polycarbonates.
19. Polysulfones and polyethersulfones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compound as crosslinking agents, and also halogen-containing modifications thereof of low flammability.
23. Thermosetting acrylic resins, derived from substituted acrylic esters, such as epoxy-acrylates, urethane-acrylates or polyester-acrylates.
24. Alkyd resins, polyester resins or acylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides and aromatic diepoxides.

26. Natural polymers, such as cellulose, rubber, gelatin and derivatives thereof which are chemically modified in a polymer-homologous manner, such as cellulose acetates, cellulose propionates and cellulose butyrates, or the cellulose ethers, such as methylcellulose.

27. Naturally occurring and synthetic organic materials which are pure monomeric compounds or mixtures of such compounds, for example mineral oils, animal and vegetable fats, oils and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

28. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

Compounds of this invention stabilize polymers especially during high temperature processing with relatively little change in color, even though the polymer may undergo a number of extrusions. Among the polymers in which this property is especially apparent are polypropylene, polyethylene, styrenics such as ABS, polyethylene- and polybutylene-terephthalates, polycarbonates, natural rubber, synthetic rubber such as SBR. While many compounds which have been used as process stabilizers are sufficiently effective as process stabilizers for polyolefins only in the presence of co-stabilizers such as phenolic antioxidants, compounds of this invention are effective in the absence of phenolic antioxidants.

Many of the compounds of this invention combine process stabilizing properties with the ability to contribute to light stability of the polymer. This is particularly important for polymer fibers where processing temperatures are among the highest and where stability to actinic light is a prime requirement. A particularly important property for stabilizers which are trivalent phosphorus esters is their non-hygroscopicity and resistance to hydrolysis in the presence of moisture in the atmosphere during ambient storage. Hygroscopicity frequently results in difficulty in incorporating the process stabilizer uniformly into the polymer causing stickiness and blockage during compounding, while hydrolysis of the phosphorus ester stabilizers during storage frequently results in compounds which are less effective.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1. Simple 2.6-dialkylphenols, such as, for example, 2,6-ditert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2. Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,6-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxy-phenyl) disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenyl], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5. O-, N- and S-benzyl compounds, such as, for example, 3,3',5,5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6. Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7. Hydroxybenzyl-aromatic compounds, such as, for example, 1,3,5-tris-(3,5-di-tert.-butyl-4-hydroxybenzyl)-2,4,6-trimethylbenzene, 1,4-bis-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8. s-Triazine compounds, such as, for example, 2,4-bis-octylmercapto-6-(3,5-di-tert.-butyl-4-hydroxy-anilino)-s-triazine, 2-octylmercapto-4,6-bis-(3,5-di-tert.-butyl-4-hydroxy-anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

1.9. Amides of β-(3,5-di-tert.-butyl-4-hydroxyphenyl) propionic acid, such as, for example, 1,3,5-tris-3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-bis-β-(3,5-di-t-butyl-4-hydroxyphenyl-propionyl)-hydrazine.

1.10. Esters of β-(3,5-di-tert.-butyl-4-hydroxyphenyl) propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.11. Esters of β(5-tert.-butyl-4-hydroxy-3-methylphenyl)propionic acid with monohydric or polyhydric alcohols, such as, for example, with methanol, ethanol, octadecanol, 1,6-hexanediol, 1,9-nonanediol, ethylene glycol, 1,2-propanediol, di-ethylene glycol, thiodiethylene glycol, neopentylglycol, penta-erythritol, 3-thia-undecanol, 3-thia-pentadecanol, trimethyl-hexanediol trimethyolethane, trimethylolpropane, tris-hydroxyethyl isocyanurate and 4-hydroxymethyl-1-phospha-2,6,7-trioxabicyclo [2,2,2]octane.

1.12. Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo [2,2,2]-octane, especially the tetra-bis ester of pentaerythritol.

1.13. Benzylphosphonates, such as, for example, dimethyl 3,5-di-tert.-butyl-4-hydroxybenzyl-phosphonate, diethyl 3,5-di-tert.butyl-4-hydroxybenzyl-phosphonate, dioctadecyl 3,5-di-tert.butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-di-phenyl-p-phenylenediamine, N,N'-di-2-naphthyl-p-phenylenediamine, N,N'-di-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline.

Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1. 2-(2'-Hydroxyphenyl)-benzotriazoles, e.g. the 5'-methyl-, 3',5'-di-tert.-butyl-, 5'-tert.butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-,α-methylbenzyl-5'-methyl-, 3'-α-methylbenzyl-5'-methyl-5-chloro, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivatives.

2.2. 2,4-bis-(2'-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzylozy-, 2',4-4'-trihydroxy- or 2'-hydroxy-4,4'-dimethoxy-derivative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenozic acid-2,4-di-tert.-butylphenyl ester or -octadecyl ester or -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or butyl ester or N-(β-carbomethoxyvinyl)-2-methyl-indoline.

2.7. Sterically hindered amines, e.g. 4-benzoyl-2,2,6,6-tetramethylpiperidine, 4-stearyl-oxy-2,2,6,6-tertramethylpiperidine, bis-(2,2,6,6-tetramethylpiperidyl)-sebacate or 3-n-octyl-7,7,9,9-tetramethyl-1,3,8-triazaspiro[4,5]decane-2,4-dione.

2.8. Oxalic acid diamides, e.g. 4,4'-di-octyloxy-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-5,4'-di-tert.-butyl-oxanilide, or mixtures of ortho and para-methoxy- as well as of o- and p-ethoxy-disubstituted oxanilides.

3. Metal deactivators, e.g. oxanilide, isophthalic acid dihydrazide, sebacic acid-bisphenylhydrazide, bis-benzylidene-oxalic acid dihydrazide, N,N'-diacetyladipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-plamitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl) phosphite, trilauryl phosphite, tri-octadecyl phosphite, 3,9-isodecyloxy-2,4,8,10-tetraoxa-3,9-diphospha spiro [5, 5]undecane and tri-(4-hydroxy-3,5-di-tert.butylphenyl) phosphite.

Other additives that can be incorporated in the stabilized compositions are thiosynergists such as dilaurylthiodipropionate or distearylthiodipropionate, lubricants such as stearyl alcohol fillers, carbon black, asbestos, kaolin, talc, glass fibers, pigments, optical brighteners, flameproofing agents and antistatic agents.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

While the instant phosphites can be beneficially used as stabilizers for a variety of substrates, particularly the polyolefins, both alone and in conjunction with other coadditives, the combination of the instant phosphites with selected hindered phenolic antioxidants exhibits enhanced and particularly salubrious protection to such substrates. The phenolic antioxidants found to be particularly useful are selected from the group consisting of 2,6-di-tert-butyl-4-methylphenol, 4,4'-thio-bis(6-tert.-butyl-3-methylphenol), 2,2'-methylene-bis(6-tert.-butyl-3-methylphenol), 2,2'-methylene-bis-(2,6-di-tert.-butylphenol), 1,1,3-tris(5-tert.-butyl4-hydroxy-2-methylphenyl)butane, 1,3,5-tris(3,5-di-tert.-butyl-4-hydroxybenzyl)-2,4,6-trimethylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentanetetrayl tertrakis(3,5-di-tert.-butyl-4-hydroxy-hydrocinnamate), 1,3,5-tris(3,5-di-tert butyl-4-hydroxybenzyl)isocyanurate, thiodiethylene bis-(3,5-di-tert-butyl-4-hydroxy hydrocinnamate and tris-(2-hydroxyethyl) isocyanate esters of β-(3,5-di-tert-butyl-4-hydroxyphenyl)propionic acid.

The compositions comprise (a) a substrate, preferably a polyolefin such as polypropylene, (b) about 0.01 to about 5% by weight of the composition and preferably about 0.025 to about 2%, and most preferably 0.025 to 1% of an instant phosphite compound or mixture thereof, and optionally, (c) a phenolic antioxidant or mixture of said antioxidants selected from the group cited directly above and also in a range of 0.01 to 5% and preferably 0.05 to 1%, by weight of the composition.

Likewise, the following light stabilizers are preferred for use, either alone or in conjunction with the listed phenolic antioxidants, as additives for incorporation with the instant stabilizers into the listed substrates: 2-(2'-hydroxy-5'-methylphenyl)benzotriazole; 2-(3',5'-di-tert-butyl-2'-hydroxyphenyl)benzotriazole; 2-(2'-hydroxy-3',5'-di-tert-amylphenyl)benzotriazole; nickel bis[O-ethyl-(3,5-di-tert-butyl-4-hydroxybenzyl)]phosphonate; bis(1,2,2,6,6-pentamethyl-4-piperidyl)-2-n-butyl-2-(3,5-di-tert-butyl-4-hydroxybenzyl) malonate; bis(2,2,6,6-tetramethyl-4-piperidyl) sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl) hexamethylene diamine.

The following examples further illustrate the embodiments of this invention. In these examples, all parts given are by weight unless otherwise specified.

EXAMPLE A

Preparation of
(3,3',5,5'-tetra-tert.-butyl-1,1'-biphenyl-2,2'diyl) phosphorochlorodite 45.21 grams of phosphorous trichloride in 50 ml of toluene were added dropwise over 85 minutes to a solution of 123.0 grams of 4,4',6,6'-tetra-tert.-butyl-2,2'-biphenol and 60.6 grams of triethylamine in about 600 ml of toluene and stirred at room temperature overnight (about 20 hours). The reaction product was filtered free from triethylamine hydrochloride, the desired product being isolated by removal of the solvent at reduced pressure to yield a solid m.p. 168°–174°.

| Analysis | % Cl |
|---|---|
| Calcd. | 7.46 |
| Found | 7.50 |

In a similar manner the following phosphorochlorodites of structure II were made.

*(2,2'-methylene-bis-[4,6-di-tert-butylphenyl]phosphorchlorodite, m.p. 207°–217° C.

*(2,2'-ethylidene-bis-[4,6-di-tert-butylphenyl]phosphorchlorodite.

*(2,2'-methylene-bis-[4,6-di-tert-amylphenyl]phosphorochloridite.

(3,3'-di-tert-butyl-5,5'-dimethyl-1,1'-biphenyl-2,2'-diyl) phosphorochlorodite.

(2,2'-methylene-bis-[4-tert-butyl-6-methylphenyl]phosphorochlorodite.

*(2,2'-n-butylidene-bis-[4,6-di-tert-butylphenyl]phosphorochlorodite.

*(3,3',5,5'-tetra-tert-octyl-1,1'-biphenyl-2,2'-diyl) phosphorochlorodite.

*(2,2'-methylene-bis-[4,6-di-tert-octylphenyl]phosphorochlorodite.

*Characterized by IR Spectra.

EXAMPLE 1

N-methyliminodiethanol-bis(3,3',5,5'-tetra-tert-butyl-1,1'-biphenyl-2,2'-diyl)phosphite A flame-dried flask under nitrogen was charged with 6.87 grams phosphorus trichloride, 10.12 grams triethyl amine, and 100 mls toluene. A solution of 20.53 grams 2,2'4,4'-tetra-tert-butyl-o,o'-bisphenol in 80 mls warm toluene was added. The reaction was heated to 40° C. until the disappearance of the hydroxyl absorption in the IR spectra. A solution of 2.98 grams 2,2'-methyliminodiethanol in 5.06 grams triethylamine was then added. The mixture was heated to 40° C. until the reaction was complete as indicated by TLC. The mixture was filtered, rotary evaporated, and recrystallized from 9:1 acetonitrile: toluene yielding 18.1 grams of a white powder (72.9% yield). M.P. 134°–140° C.

Analysis: Calculated for $C_{61}H_{91}NO_6P_2$: C, 73.54; H, 9.21; N, 1.41. Found: C, 73.63; H, 8.93; N, 1.37.

EXAMPLE 2

N-methyliminodiethanol-bis[2,2'-methylene-bis (4,6-di-tert.-butylphenyl-2,2'-diyl)]phosphite The procedure of Example 1 was repeated using 6.87 grams phosphorus trichloride, 15.18 grams triethylamine, 21.27 grams 2,2'-methylene-bis(4,6-di-tert.-butylphenol) and 2.98 grams N-methyliminodiethanol.

The reaction product was recrystallized twice from 95:5 heptane: toluene, yielding a white powder M.P. 219°–221° C. Analysis: Calculated for $C_{63}H_{95}NO_6P_2$: C, 73.87; H, 9.35; N, 1.37. Found: C, 73.88; H, 9.49; N, 1.37.

EXAMPLE 3

2,2′,2″-Nitrilotriethanol-tris-[2,2′-methylene-bis-(4,6-di-tert.-butylphenyl-2,2′-diyl)]-phosphite The procedure of Example 1 was followed using 8.24 grams phosphorus trichloride, 18.21 grams triethylamine, 25.48 grams 2,2′-methylene-bis(4,6-di-tert.-butylphenol), and 2.98 grams triethanolamine. The reaction product was recrystallized from 2-butanone yielding a white powder M.P. 177°–181° C. Analysis: Calculated for $C_{93}H_{138}NO_9P_3$: C, 74.12; H, 9.23; N, 0.93. Found: C, 74.17; H, 9.10; N, 0.79.

EXAMPLE 4

2,2′,2″-Nitrilotriethanol-tris-(3,3′,5,5′-tetra-tert.-butyl-1,1′-biphenyl-2,2′-diyl)-phosphite The procedure of Example 1 was repeated using 6.87 grams phosphorus trichloride, 15.18 grams triethylamine, 20.53 grams 2,2′, 4,4′-tetra-tert.-butyl-o,o′-biphenol and 2.49 grams triethanolamine. The reaction product was recrystallized twice from acetonitrile: toluene yielding a white powder. M.P. 121°–134° C. Analysis: Calculated for $C_{90}H_{132}NO_9P_3$; C, 73.79; H, 9.08; N, 0.96. Found: C, 73.89; H, 8.79; N, 1.06.

EXAMPLE 5

N,N-Dimethylaminoethyl-o,o-(3,3′,5,5′-tetra-tert.-butyl-1,1′-biphenyl-2,2′-diyl)phosphite The procedure of Example 1 was followed using 6.87 grams phosphorus trichloride, 15.10 grams triethylamine, 20.50 grams 2,2′,4,4′-tetra-tert.-butyl-o,o′-biphenol, and 4.46 grams N,N′-dimethylethanolamine. The reaction product was recrystallized twice from acetonitrile yielding a white powder M.P. 120°–125° C. Analysis: Calculated for $C_{32}H_{50}NO_3P$; C, 72.83; H, 9.55; N, 2.65. Found: C, 72.79; H, 9.66; N, 2.71.

EXAMPLE 6

2,2′,2″-Nitrilotriethanol-tris-[2,2′-ethylidene-bis-(4,6-di-tert-butylphenyl)]phosphite The procedure of Example 1 was followed using 13.75 grams phosphorus trichloride, 30.36 grams triethylamine, 43.87 grams 2,2′-ethylidene-bis (4,6-di-tert-butylphenol) and 4.97 grams triethanolamine. The reaction product was recrystallized from 2-butanone yielding a white powder. M.P. 241°–246° C. Analysis: Calculated for $C_{96}H_{144}NO_9P_3$; C, 74.43; H, 9.37; N, 0.90. Found: C, 74.76; H, 9.37; N, 0.85.

EXAMPLE 7

N-methyliminodiethanol-bis-[2,2′-ethylidene-bis(4,6-di-tert-butylphenyl]phosphite The procedure of Example 1 was followed using 27.47 grams triethylamine, 87.74 grams 2,2′-ethylidene-bis (4,6-di-tertbutyl-phenol), and 11.92 grams 2,2′-methyliminodiethanol. The reaction product was recrystallized from 1:1 acetonitrile: toluene yielding a white powder. M.P. 246°–254° C. Analysis: Calculated for $C_{65}H_{99}NO_6P_2$; C, 74.18; H, 9.48; N, 1.33. Found: C, 74.44; H, 9.53; N, 1.43.

EXAMPLE 8

2,2′,2″-Nitrilotri-2-propanol-tris-[2,2′-methylene-bis(4,6-di-tert-butylphenyl)]phosphite.

The procedure of Example 1 was followed using 27.47 grams phosphorus trichloride, 60.72 grams triethylamine, 84.93 grams 2,2′-methylene-bis(4,6-di-tert-butylphenol), and 12.76 grams 1,1′, 1″-nitrilotri-2-propanol. The reaction product was recrystallized from acetone and 2-butanone yielding a white powder M.P. 173°–178° C. Analysis: Calculated for $C_{96}H_{144}NO_9P_3$; C, 74.43; H, 9.37; N, 0.90. Found: C, 74.38; H, 9.05; N, 0.84.

EXAMPLE 9

2,2′,2″-Nitrilotri-2-propanol-tris[2,2′-ethylene-bis(4,6-di-tert.-butylphenyl)]phosphite The procedure of Example 1 was followed using 27.47 grams phosphorus trichloride, 60.72 grams triethylamine, 87.74 gram 2,2′-ethylidenebis(4,6-di-tert-butylphenol), and 12.76 grams 1,1′1″-nitrilotri-2-propanol. The reaction product was recrystallized from acetone and acetone-toluene yielding a white powder. M.P. 165°–170° C. Analysis: Calculated for $C_{99}H_{150}NO_9P_3$; C, 74.73; H, 9.50; N, 0.88. Found: C, 74.66; H, 9.22; N, 0.95.

Following the procedure of Example 1, the following compounds were made having the structure as shown in III, the symbols being defined in TABLE I.

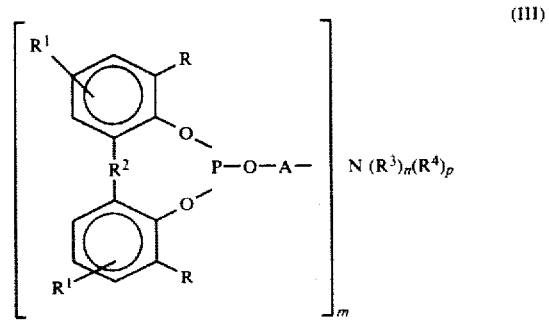

(III)

TABLE 1

| Example No. | $R^1$ | R | $R^2$ | m | $R^3$ and/or $R^4$ | n | p | A | M.P. °C. |
|---|---|---|---|---|---|---|---|---|---|
| 10 | $(CH_3)_3C-$ | $(CH_3)_3C-$ | — | 2 | $CH_3(CH_2)_3-$ | 1 | 0 | $-CH_2-CH_2-$ | 163–165 |
| 11 | $(CH_3)_3C-$ | $(CH_3)_3C-$ | $-CH_2-$ | 2 | $CH_3(CH_2)_3-$ | 1 | 0 | $-CH_2-CH_2-$ | 213–215 |
| 12 | $CH_3\!\!\diagdown\!\!C_2H_5\!-\!\!C\!-\!\diagup\!\!CH_3$ | $CH_3\!\!\diagdown\!\!C_2H_5\!-\!\!C\!-\!\diagup\!\!CH_3$ | $-CH_2-$ | 2 | $CH_3-$ | 1 | 0 | $-CH_2-CH_2-$ | 147–150 |
| 13 | $CH_3\!\!\diagdown\!\!C_2H_5\!-\!\!C\!-\!\diagup\!\!CH_3$ | $CH_3\!\!\diagdown\!\!C_2H_5\!-\!\!C\!-\!\diagup\!\!CH_3$ | $CH_2$ | 3 | — | 0 | 0 | $-CH_2-CH_2-$ | 206–210 |

TABLE 1-continued

| Example No. | $R^1$ | R | $R^2$ | m | $R^3$ and/or $R^4$ | n | p | A | M.P. °C. |
|---|---|---|---|---|---|---|---|---|---|
| 14 | $(CH_3)_3C-$ | $(CH_3)_3C-$ | $CH_3$<br>\|<br>$-CH-$ | 2 | $(CH_2(CH_2)_3-$ | 1 | 0 | $-CH_2-CH_2-$ | 190–92 |
| 15 | $CH_3$<br>\\H<br>$C_2H_5-C-$ | $(CH_3)_3C-$ | $CH_3$<br>\|<br>$-CH-$ | 2 | $CH_3-$ | 1 | 0 | $-CH_2-CH_2-$ | 227–32 |
| 16 | $(CH_3)_3C-$ | $(CH_3)_3C-$ | $CH_3$<br>\|<br>$-CH-$ | 1 | $C_2H_5-$ | 1 | 1 | $-CH_2-CH_2-$ | 153–155 |
| 17 | $CH_3$<br>\\<br>$C_2H_5-C-$<br>/<br>$CH_3$ | $CH_3$<br>\\<br>$C_2H_5-C-$<br>/<br>$CH_3$ | $CH_3$<br>\|<br>$-CH-$ | 2 | $CH_3-$ | 1 | 0 | $-CH_2-CH_2-$ | 160–72 |
| 18 | t-octyl- | t-octyl | — | 2 | $CH_3-$ | 1 | 0 | $-(CH_2)_6-$ | |
| 19 | $n-C_{18}H_{37}-$ | $n-C_{18}H_{37}$ | $-CH_2-$ | 1 | $CH_3-$ | 1 | 1 | $-(CH_2)_3-$ | |
| 20 | $CH_3-$ | $(CH_3)_3C-$ | $-CH_2-$ | 3 | — | 0 | 0 | $\left(\begin{array}{c}-CH_2-CH-\\ \| \\ CH_3\end{array}\right)$ | |

EXAMPLE 20

Processing Stability of Polypropylene

Base Formulation:

| Polypropylene* | 100 parts |
|---|---|
| Calcium stearate | 0.10 parts |

*Profax 6501 from Hercules Chemical

Stabilizers were solvent blended into polypropylene as solutions in methylene chloride and, after removal of the solvent by evaporation at reduced pressure, the resin was extruded using the following extruder conditions:

| | Temperature (°C.) |
|---|---|
| Cylinder #1 | 232 |
| Cylinder #2 | 246 |
| Cylinder #3 | 260 |
| Die #1 | 260 |
| Die #2 | 260 |
| Die #3 | 260 |
| RPM | 100 |

During extrusion, the internal extruder pressure was determined using a pressure transducer. After each of the first, third and fifth extrusions, resin pellets were compression molded into 125 mil (3.2 mm) thick plaques at 193° C. and specimen yellowness index (Y.I.) determined according to ASTM D1925-63T.

The melt flow rate (MFR) was determined by ASTM method 1238 condition L. The melt flow rate varies inversely as the transducer pressure and both are a measure of the molecular weight for a specific type of polymer. The results are shown in Table II.

TABLE II

Extrusion Temp. - 260° C.

| ADDITIVE | | TRANSDUCER PRESSURE AFTER EXTRUSION (psi) | | | MFR (g/10MIN) AFTER EXTRUSION | | | YI COLOR AFTER EXTRUSION | | |
|---|---|---|---|---|---|---|---|---|---|---|
| | | 1 | 3 | 5 | 1 | 3 | 5 | 1 | 3 | 5 |
| None | | 525 | 450 | 375 | 6.4 | 12.0 | 10.6 | 6.1 | 7.7 | 8.6 |
| 0.1% | Antioxidant A* | 570 | 570 | 525 | 3.5 | 5.3 | 6.6 | 8.5 | 11.6 | 15.1 |
| 0.1% Antioxidant A* and a compound as indicated below. | | | | | | | | | | |
| 0.05% | Ex. 2 | 675 | 690 | 645 | 2.9 | 3.1 | 3.7 | 8.2 | 9.7 | 10.6 |
| 0.05% | Ex. 1 | 675 | 705 | 660 | 2.5 | 2.7 | 3.4 | 7.7 | 8.8 | 9.8 |
| 0.05% | Ex. 3 | 660 | 690 | 645 | 2.4 | 2.9 | 3.6 | 7.3 | 10.1 | 10.6 |
| 0.05% | Ex. 4 | 675 | 705 | 660 | 2.3 | 3.0 | 3.6 | 7.7 | 9.0 | 10.1 |

*Antioxidant A is neopentanetetrayl tetrakis -[3-(3',5'-di-tert.-butyl-4'-hydroxyphenyl) propionate]

Similarly, stabilizers of this invention were blended into Profax 6501 as described above and the formulated resin was extruded at 288° C. using the following extruder conditions:

| | Temperature (°C.) |
|---|---|
| Cylinder #1 | 260 |
| Cylinder #2 | 274 |
| Cylinder #3 | 288 |
| Die #1 | 288 |
| Die #2 | 288 |
| Die #3 | 288 |
| RPM | 100 |

The results are shown in Table III.

TABLE III

Extrusion Temp. - 288° C.

| ADDITIVE | | TRANSDUCER PRESSURE AFTER EXTRUSION (psi) | | | MFR (g/10MIN) AFTER EXTRUSION | | | YI COLOR AFTER EXTRUSION | | |
|---|---|---|---|---|---|---|---|---|---|---|
| | | 1 | 3 | 5 | 1 | 3 | 5 | 1 | 3 | 5 |
| None | | 400 | 225 | 150 | 7.9 | 35.8 | 78.5 | 6.2 | 6.6 | 6.4 |
| 0.1% | Antioxidant A* | 445 | 390 | 300 | 5.9 | 10.2 | 15.6 | 9.2 | 10.6 | 12.5 |
| 0.1% | Ex. 1 | 535 | 480 | 405 | 3.5 | 6.2 | 9.8 | 6.1 | 6.4 | 6.7 |

TABLE III-continued

| | | \multicolumn{3}{c}{Extrusion Temp. - 288° C.} | | | | | |
|---|---|---|---|---|---|---|---|---|---|
| ADDITIVE | | TRANSDUCER PRESSURE AFTER EXTRUSION (psi) | | | MFR (g/10MIN) AFTER EXTRUSION | | | YI COLOR AFTER EXTRUSION | | |
| | | 1 | 3 | 5 | 1 | 3 | 5 | 1 | 3 | 5 |
| 0.1% | Ex. 4 | 525 | 495 | 405 | 3.8 | 6.2 | 9.0 | 5.9 | 6.6 | 6.9 |
| 0.1% | Ex. 14 | 510 | 540 | 450 | 3.0 | 5.3 | 9.6 | 6.3 | 7.2 | 6.9 |
| 0.1% | Ex. 3 | 495 | 510 | 405 | 3.7 | 5.6 | 9.2 | 6.8 | 6.9 | 7.2 |
| 0.1% | Ex. 2 | 540 | 520 | 405 | 3.6 | 6.2 | 10.7 | 6.3 | 6.9 | 7.7 |
| 0.1% Antioxidant A* and a compound as indicated below. | | | | | | | | | | |
| 0.05% | Ex. 1 | 525 | 600 | 480 | 3.3 | 4.1 | 5.8 | 8.2 | 9.2 | 10.6 |
| 0.05% | Ex. 4 | 525 | 605 | 525 | 3.1 | 4.2 | 5.0 | 7.4 | 9.3 | 9.6 |
| 0.05% | Ex. 14 | 520 | 585 | 465 | 2.8 | 3.7 | 5.0 | 7.9 | 8.5 | 9.1 |
| 0.05% | Ex. 3 | 510 | 580 | 480 | 3.5 | 4.6 | 6.0 | 8.2 | 9.5 | 10.1 |
| 0.05% | Ex. 2 | 525 | 580 | 510 | 3.3 | 4.6 | 6.4 | 7.9 | 9.0 | 10.0 |

*Antioxidant A is neopentanetetrayl tetrakis -[3-(3',5'-di-tert.-butyl-4'-hydroxyphenyl) propionate]

What is claimed is:

1. A compound of the formula

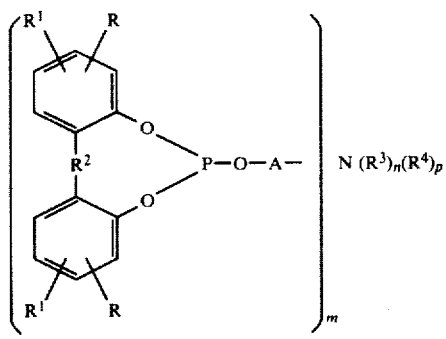

wherein m, n and p are each 1, m is 2 and n is 1 and p is 0 or m is 3 and n and p are 0, and wherein R is alkyl of from 1 to 18 carbon atoms, $R^1$ is hydrogen or alkyl of from 1 to 18 carbon atoms, $R^2$ is a direct bond or alkylene of from 1 to 12 carbon atoms, A is alkylene of from 1 to 6 carbon atoms, or cycloalkylene of 5 to 6 carbon atoms, $R^3$ is alkyl of 1 to 18 carbon atoms, or

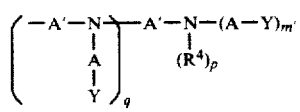

wherein Y is

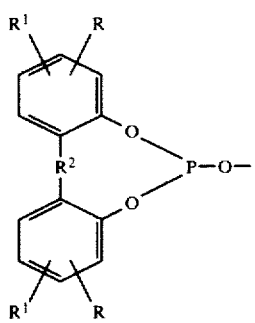

A' is alkylene of 1 to 6 carbon atoms or cycloalkylene of 5 to 6 carbon atoms, m' is 1 or 2, p is 0 or 1, and q is 0-5, with A, R, $R^1$, $R^2$ being as previously defined; provided that when p and q are 0, —N—A'—N can be a diazacycloalkyl group of 2 to 10 carbon atoms, or when m is 1 and p is 0, N—$R_3$ is a azacycloalkyl group of 2 to 10 carbon atoms or an azaoxacycloalkyl group of 3 to 7 carbon atoms; and $R^4$ is alkyl of 1 to 18 carbon atoms.

2. The compound of claim 1, wherein R is in the ortho position to the phosphite oxygen in each of the phenyl rings.

3. The compound of claim 2, wherein R is alkyl of from 4 to 8 carbon atoms.

4. The compound of claim 3, wherein R is tert. butyl, tert. pentyl or tert. octyl.

5. The compound of claim 2, wherein $R^1$ is tert. alkyl of from 4 to 8 carbon atoms.

6. The compound of claim 2, wherein $R^2$ is alkylene of the formula

wherein $R^5$ and $R^6$ are independently hydrogen, alkyl of from 1 to 7 carbon atoms or aryl, provided that the total number of carbon atoms does not exceed 12.

7. N-Methyliminodiethanol-bis(3,3',5,5'-tetra-tert-butyl-1,1'-biphenyl-2,2'-diyl) phosphite according to claim 2.

8. N-Methyliminodiethanol-bis[2,2'-methylene-bis(4,6-di-tert.-butylphenyl)]phosphite according to claim 2.

9. 2,2',2"-Nitrilotriethanol-tris[2,2'-methylenebis(4,6-di-tert-butylphenyl)]phosphite according to claim 2.

10. 2,2',2"-Nitrilotriethanol-tris-(3,3',5,5'-tetra-tert.-butyl-1,1'-biphenyl-2,2'-diyl)phosphite according to claim 2.

11. N,N-dimethylaminoethyl-o,o-(3,3',5,5'-tetra-tert.-butyl-1,1'-biphenyl-2,2'-diyl)phosphite according to claim 2.

12. 2,2',2"-Nitrilotriethanol-tris-[2,2'-ethylidene-bis(4,6-di-tert.-butylphenyl)]phosphite according to claim 2.

13. N-Methyliminodiethanol-bis[2,2'-ethylidene-bis(4,6-di-tert.-butylphenyl)]phosphite according to claim 2.

14. 2,2',2''-Nitrilotri-2-propanol-tris[2,2'-methylene-bis(4,6-di-tert.-butylphenyl)]phosphite according to claim 2.

15. 2,2',2''-Nitrilotri-2-propanol-tris[2,2'-ethylene-bis(4,6-di-tert.-butylphenyl)]phosphite according to claim 2.

16. A composition of matter comprising an organic material subject to oxidative, thermal and actinic degradation stabilized with an effective stabilizing amount of a compound of claim 1 or 2.

17. The composition of claim 16, wherein the organic material is a synthetic polymer.

18. The composition of claim 17, wherein said synthetic polymer is a polyolefin homopolymer or copolymer.

19. The composition of claim 18, wherein said polyolefin is selected from the group consisting of polyethylene, polypropylene, polyisobutylene, poly(butene-1), poly(pentene-1), poly(methylbutene-1) and poly(4-methylpentene-1).

20. The composition of claim 17, wherein said polymer is selected from the group consisting of polystyrene, acrylonitrile/butadiene/styrene, styrene/butadiene rubber, polyesters, polyurethanes, polycarbonates, polyamides and polysulfones.

21. The composition of claim 16 which also contains a phenolic antioxidant selected from the group consisting of 2,6-di-tert-butyl-4-methylphenol, 4,4'-thio-bis(6-tert-butyl-3-methylphenol),2,2'-methylene-bis(6-tert-butyl-4-methylphenol), 4,4'-methylene-bis(2,6-di-tert-butylphenol), 1,1,3'-tris(5-tert-butyl-4-hydroxy-2-methylphenyl)butane, 1,3,5-tris(3,5-di-tert-butyl-4-hydroxybenzyl)-2,4,6-trimethylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentane-tetrayl tetrakis(3,5-di-tert-butyl-4-hydroxy-hydrocinnamate), 1,3,5-tris(3,5-di-tert-butyl-4-hydroxybenzyl) isocyanurate, thiodiethylene bis(3,5-di-tert-butyl-4-hydroxy-hydrocinnamate) and tris(2-hydroxyethyl)isocyanate ester of β-(3,5-di-tert-butyl-4-hydroxyphenyl)propionic acid.

22. The composition of claim 16 which also contains a light stabilizer selected from the group consisting of 2-(2'-hydroxy-5'-methylphenyl)benzotriazole; 2-(3',5'-di-tert-butyl-2'-hydroxyphenyl)benzotriazole; 2-(2'-hydroxy-3',5'-di-tert-amylphenyl)benzotriazole; nickel bis[O-ethyl-(3,5-di-tert-butyl-4-hydroxybenzyl)]phosphonate; bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl)sebacate; di-methyl-succinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

23. The composition of claim 21 which also contains a light stabilizer selected from the group consisting of 2-(2'-hydroxy-5'-methylphenyl)benzotriazole; 2-(3', 5'-di-tert-butyl-2'-hydroxyphenyl)benzotriazole; 2-(2'-hydroxy-3,',5'-di-tert-amylphenyl)benzotriazole; nickel bis[O-ethyl-(3,5-di-tert-butyl-4-hydroxybenzyl)]phosphonate; bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl)sebacate; di-methyl-succinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

24. A method for stabilizing an organic material against oxidative, thermal and actinic degradation which comprises incorporating into said organic material an effective stabilizing amount of a compound of claim 1 or 2.

* * * * *